(12) United States Patent
Deco et al.

(10) Patent No.: US 7,006,866 B1
(45) Date of Patent: Feb. 28, 2006

(54) ARRANGEMENT FOR PREDICTING AN ABNORMALITY OF A SYSTEM AND FOR CARRYING OUT AN ACTION WHICH COUNTERACTS THE ABNORMALITY

(75) Inventors: Gustavo Deco, München (DE); Louis-J. Dubé, Sillery (CA)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/530,983

(22) PCT Filed: Nov. 5, 1998

(86) PCT No.: PCT/DE98/03229

§ 371 (c)(1),
(2), (4) Date: May 8, 2000

(87) PCT Pub. No.: WO99/24884

PCT Pub. Date: May 20, 1999

(30) Foreign Application Priority Data

Nov. 7, 1997 (DE) ................................. 197 49 373

(51) Int. Cl.
*A61N 1/08* (2006.01)
(52) U.S. Cl. ............................................ 607/5; 706/20
(58) Field of Classification Search ................ 128/925; 600/14, 374, 377, 378, 382, 383, 509, 513, 600/515, 518, 519, 544; 607/4, 5, 7, 9, 14, 607/17, 62, 119; 700/38, 40, 45; 706/20, 706/21, 23
See application file for complete search history.

(56) References Cited

U.S. PATENT DOCUMENTS

| | | | |
|---|---|---|---|
| 4,889,526 A | | 12/1989 | Rauscher et al. |
| 5,092,343 A | * | 3/1992 | Spitzer et al. ............... 128/733 |
| 5,251,626 A | | 10/1993 | Nickolls et al. |
| 5,465,321 A | * | 11/1995 | Smyth .......................... 395/22 |
| 5,782,885 A | * | 7/1998 | Andersson ..................... 607/17 |
| 5,862,304 A | * | 1/1999 | Ravdin et al. ................. 395/22 |
| 5,995,863 A | * | 11/1999 | Farace et al. ............... 600/410 |
| 6,117,066 A | * | 9/2000 | Abrams et al. ............... 600/14 |

FOREIGN PATENT DOCUMENTS

| | | |
|---|---|---|
| DE | 43 37 110 | 11/1994 |
| DE | 196 04 803 | 10/1996 |
| DE | 195 31 967 | 9/1997 |
| WO | WO 95/10075 | 4/1995 |
| WO | WO 96/36860 | 11/1996 |

OTHER PUBLICATIONS

L. Machado et al., "Sequential Versus Standard Neural Networks For Pattern Recognition: An Example Using The Domain Of Coronary Heart Disease", Computers in biology & medicine; vol. 27, No. 4, Jul. (1997), pp. 267-281, XP002097626.

(Continued)

*Primary Examiner*—Robert E. Pezzuto
*Assistant Examiner*—Frances P. Oropeza
(74) *Attorney, Agent, or Firm*—Staas & Halsey LLP

(57) ABSTRACT

An arrangement and method are presented that enable a prediction of an abnormality and implement a suitable action opposing the abnormality. An information flow underlying a dynamic system is interpreted and a prediction quantity that comprises the abnormality as characterizing quantity of the dynamic system is determined from it. A neural network is trained with measured data of the system. After the training, the abnormality can be indicated on the basis of the prediction quantity before it occurs and the occurrence can be opposed with suitable measures.

18 Claims, 2 Drawing Sheets

OTHER PUBLICATIONS

G. Deco et al., "Determining the Information Flow of Dynamical Systems from Continuous Probability Distributions", The American Physical Society, Physical Review Letters, vol. 78, No. 12, Mar. (1997), pp. 2345-2348.

C. Schittenkopf et al., Testing nonlinear Markovian hypotheses in dynamical systems, Physica D104, (1997), pp. 61-74.

J. Herz et al., "Introduction to the Theory of Neural Computation", Lecture Notes vol. 1, (1991), pp. 197-250.

G. Deco et al., "An Information Theoretic Approach to Neural Computing", Chapter 7, (1996) pp. 170-186.

B. Gluckman, et al., Electric Field Suppression of Epileptiform Activity in hippocampal Slices, Rapid Publication, Journal of Neurophysiology 76, (1996), pp. 4202-4205.

* cited by examiner

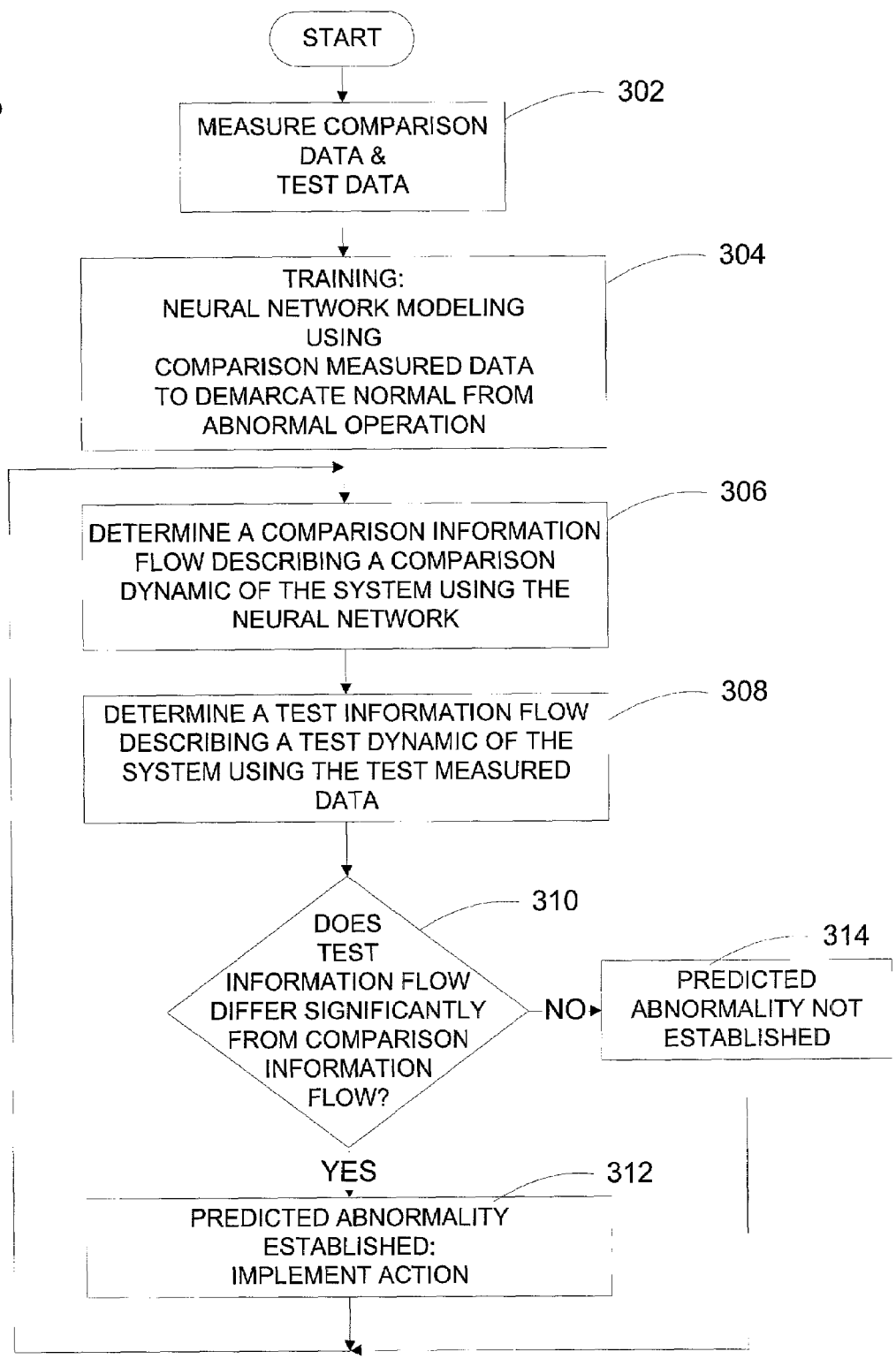

ARRANGEMENT FOR PREDICTING AN ABNORMALITY OF A SYSTEM AND FOR CARRYING OUT AN ACTION WHICH COUNTERACTS THE ABNORMALITY

BACKGROUND OF THE INVENTION

1. Field of the Invention

The invention is directed to an arrangement for predicting an abnormality of a system and for the implementation of an action opposing the abnormality.

2. Description of the Related Art

The determination of an information flow of a system is known from G. Deco, C. Schittenkopf and B. Schürmann, "Determining the information flow of dynamical systems from continuous probability distributions", Phys. Rev. Lett. 78, pages 2345–2348, 1997 (Deco), and C. Schittenkopf and G. Deco, "Testing non-linear Markovian hypotheses in dynamical systems", Physica D104, pages 61–74, 1997 (Schittenkopf).

The information flow described in these references characterizes a loss of information in a dynamic system and describes decaying statistical dependencies between the entire past and a point in time that lies p steps in the future as a function of p. Among other things, the utility of such an information flow is that a dynamic behavior of a complex system can be classified, allowing a suitable parameterized model to be found that enables a modelling of data of the complex dynamic system.

A neural network and the training of a neural network are known from J. Herz, A. Krogh, R. Palmer, "Introduction to the Theory of neural computation", Addision-Wesly, 1991 (Herz).

SUMMARY OF THE INVENTION

The object of the invention is to provide an arrangement that, enables a prediction of an abnormality of a system and then implements an action opposing the abnormality.

This object is achieved by an arrangement for predicting an abnormality of a dynamic system and for implementing an action opposing the abnormality, comprising:
 a) a measured data pick-up that registers comparison measured data of the system and test measured data of the system;
 b) a processor unit, having a neural network that models the system, the processor:
  (1) training the neural network using the comparison measured data;
  (2) determining a comparison information flow that describes a comparison dynamic of the system using the trained neural network;
  (3) determining a test information flow that describes a test dynamic of the system using the test measured data;
  (4) using the comparison information flow and of the test information flow, predicting the abnormality as established when the comparison information flow differs significantly from the test information flow and predicting the abnormality as not established when the comparison information flow does not significantly differ from the test information flow;
  (5) when the abnormality of the system has been predicted as established, then implementing the action, and
 c) an actuator that implements the action.

This object is also achieved by a method for predicting an abnormality of a dynamic system and for implementing an action opposing the abnormality, comprising the steps of:
 a) measuring comparison measured data of the system and test measured data of the system;
 b) determining a neural network that models the system using of the comparison measured data;
 c) determining a comparison information flow that describes a comparison dynamic of the system using the neural network;
 d) determining a test information flow that describes a test dynamic of the system using the test measured data;
 e) comparing the comparison information flow to the test information flow using the comparison information flow and of the test information flow;
 f) determining the abnormality to be predicted as established when the comparison information flow differs significantly from the test information flow;
 g) determining the abnormality to be predicted as not established when the comparison information flow does not significantly differ from the test information flow; and
 h) implementing the action when the abnormality of the system has been predicted as established.

Finally, this object is achieved by a method for predicting an abnormality of a dynamic system, comprising the steps of:
 a) measuring comparison measured data of the system and test measured data of the system;
 b) determining a comparison information flow that describes a comparison dynamic of the system using the comparison measured data;
 c) determining a test information flow that describes a test dynamic of the system using the test measured data;
 d) comparing the comparison information flow to the test information flow using the comparison information flow and of the test information flow;
 e) determining the abnormality to be predicted as established when the comparison information flow differs significantly from the test information flow;
 f) determining the abnormality to be predicted as not established when the comparison information flow does not significantly different from the test information flow.

An arrangement for predicting an abnormality of a system and for implementing an action opposing the abnormality is inventively recited that has a measured data pick-up that determines measured data of the system. A processor implements the following steps:
 (1) a neural network is trained on the basis of the measured data;
 (2) the information flow of the system is used to make a prediction about anticipated measured data;
 (3) when the prediction indicates that the abnormality of the system is anticipated, the action is implemented.

An actuator that implements the action is provided in the arrangement that depends on the respective application.

A goal of the invention is to provide a systematic approach to the general problem, to derive a solution of this general problem from it and to determine a quantity (referred to below as prediction quantity) that is suitable for predicting dynamic events of a system. The early recognition of a pattern that represents an abnormality in a "normal" behavior of the system is of great significance, as, among other things, the following applied examples document.

The applied strategy is divided into three steps:
1. The dynamically characterizing features of the system are extracted and adaptively learned (trained). The measure for learning the dynamics of the system in this dynamic learning phase should be general enough to correspond to stationary as well as non-stationary conditions. The dynamic learning phase is also used in order to demarcate a normal condition of the system from an abnormal condition (abnormality).
2. At least one variable (prediction quantity) is determined with which the abnormality is successfully described.
3. As soon as an occurrence of the abnormality is indicated, the information of the impending abnormality is used in order to oppose the impending abnormality via an actuator whose job is to restore the dynamic system into the normal condition. One also considers that the normal condition is subject to a natural modification over the course of time; this is taken into consideration by adaption, i.e., continued training of the neural network even after the learning phase.

One development endlessly loops through steps (2) and (3) of the processor unit.

Another development of the invention is deals with the situation where the predetermined abnormality is an information flow with a dynamic value below a prescribable threshold. In this case, the action can be comprised of supplying the system with noise.

It is possible to deliver this noise on the basis of a corresponding electrical field or a corresponding magnetic field. Both the electrical field as well as the magnetic field can be supplied to the system using at least one electrode.

An additional improvement deals with a situation where the predetermined abnormality is an information flow having a dynamic value above a predetermined threshold. The system may be excited, in reaction, with a regular signal. This can take place on the basis of an electrical or magnetic field. The electrical field and/or the magnetic field can be respectively supplied to the system using at least one electrode.

In the framework of another development, it is also possible to utilize an electrical and a magnetic field in combination in order to oppose the abnormality.

Developments of the invention are discussed below.

BRIEF DESCRIPTION OF THE DRAWINGS

Exemplary embodiments of the invention are presented in greater detail on the basis of the following Figures.

FIG. 3 is a flowchart showing steps of a method for implementation on a processor unit.

DETAILED DESCRIPTION OF THE PREFERRED EMBODIMENTS

The measured data pick-up MDA registers measured data of a system S. To this end, the measured data pick up MDA is preferably arranged within the system S in order to register the measured data on site. The measured data are conducted to a processor unit PRE where they are processed. The processor unit PRE preferably comprises a neural network NN that, following training, suitably interprets further measured data registered by the measured data pick-up MDA. When there are indications that an action is to be implemented due to the measured data, an actuator AKT is initiated by the processor unit PRE to implement a predetermined action. The actuator preferably comprises at least one electrode that is directly driven by the processor unit PRE.

Figure 1:
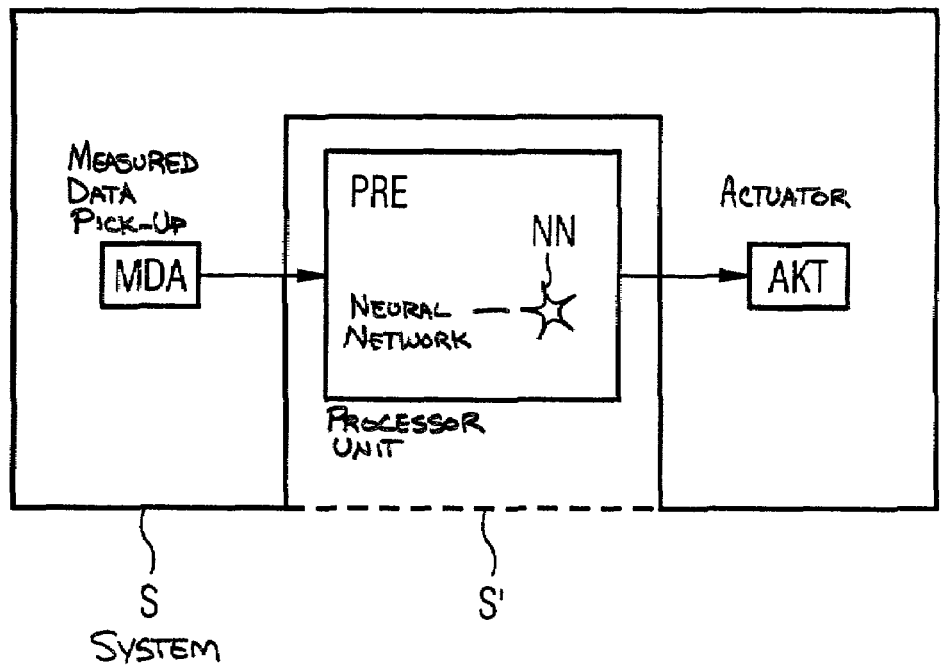
FIG. 1 is a block diagram showing an arrangement for predicting an abnormality of a system and for implementing an action opposing the abnormality.

The processor unit is arranged in the system S', as indicated in FIG. 1 on the basis of the broken line and the appertaining designation of the system S'.

The system S preferably comprises the measured data pick-up MDA and/or the actuator AKT in order to respectively assure a direct access of the measured data pick-up MDA to the measured data and of the actuator AKT to the system.

Figure 2:
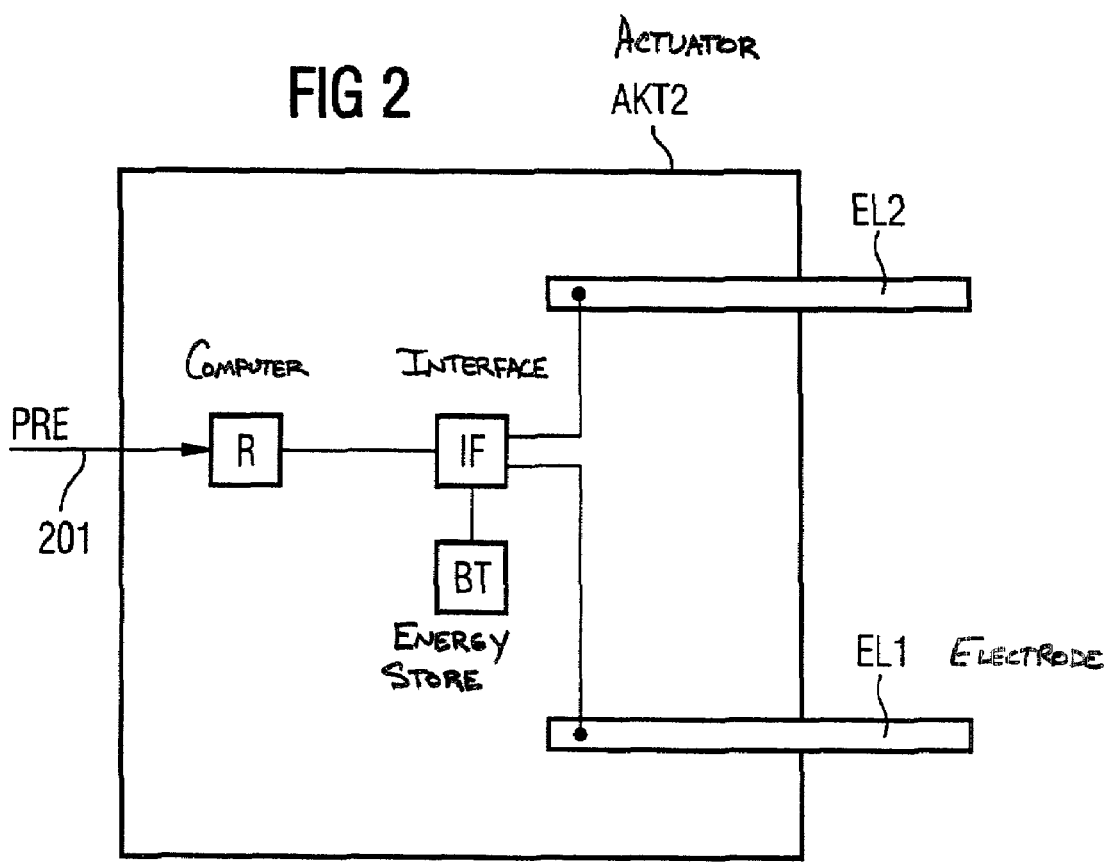
FIG. 2 is a block diagram showing an actuator AKT2, an active component, composed of a computer R, an interface IF, an energy store BT and two electrodes EL1 and EL2.

FIG. 2 shows a differently constructed actuator AKT 2. This actuator AKT2 likewise receives a signal from the processor unit PRE, via the interface 201, that informs a computer R, which is part of the actuator AKT2, that a predetermined action is to be implemented. Furthermore, an energy store BT is provided in the actuator AKT2. This energy store BT, controlled by the computer R, applies energy to the electrodes EL1 and EL2 in a suitable way. The computer R of the actuator AKT2 controls the interface IF in order to preferably determine amplitude and frequency of the energy applied to the electrodes EL1 and EL2.

FIG. 3 shows steps of the method implemented by the processor unit PRE.

A neural network NN is trained as follows. Both comparison data and test data are measured using the measured data pick-up MDA in process 302. The neural network NN is modeled based on the comparison measured data in process 304. This modeling is used to demarcate normal operation from abnormal operation, and permits a later determination of whether newly measured data indicates an abnormality in the system. After the ending of the training, information flows according to Deco or Schittenkoph are evaluated. A comparison information flow describing a comparison dynamic of the system is determined using the trained neural network NN in process 306. A test information flow describing a test dynamic of the system is determined using the test measured data in process 308. A comparison as to whether the test information flow differs significantly, according to some predetermined criteria, from the comparison information flow is performed in decision 310. If the comparison difference is significant, this is indicative of an abnormality that is predicted—such an abnormality of the system can be indicated on the basis of this information flow before the occurrence of this abnormality. When a predicted abnormality is established, an action that opposes an occurrence of the abnormality is implemented in process 312, and a branch is made preferably to process 306. If the comparison difference is not significant, then the predicted abnormality is not established, and no action is implemented, a branch is made preferably to process 306.

Two applied examples follow, that illustrate the possibilities of a prediction of an abnormality.

Application 1: Electrocardiogram (ECG) Data

One application relates to the possible prediction of a fibrillating heart. The abnormality occurs when the heart beats nearly chaotically.

ECG measured data are inventively employed in order to learn the dynamics of a heart of a patient (the training phase of the neural network NN). The dynamics of the heart vary greatly dependent, for example, on the time of day and the activity in which a person is engaged at a particular moment. Invariable quantities (prediction quantity) that significantly describe the dynamics of the heart of a person despite great variation are nonetheless determined. A variation of the prediction quantity enables the prediction of an abnormality of the heart. A control mechanism that restores the normal heart rhythm is started upon recognition of the abnormality.

The prediction quantity represents an imaging of a sudden variation of the complexity of the dynamics, and the actuator is realized in the form of an electrode that delivers small electrical pulses to the heart.

Application 2: Electroencephalogram (EEG) Data

The brain, (e.g., a human brain) is another dynamic system. When it is assumed that EEG measured data represent brain activity, one task is to suitably interpret the signals and potentially link predetermined measures to them. An epileptic attack is characterized by a synchronous firing of a group of neurons that are arranged centered around a mid-point. This synchronism reduces the complexity of the dynamics of the brain and is indicated by EEG measured data. In contrast to this, the normal condition, i.e., the normally working brain, represents a condition of irregularly firing neurons.

The early recognition of an epileptic attack becomes possible by determining a continued simplification of the dynamics of the brain. The actuator for restoring the normal condition has the job of opposing this synchronism that is apparently responsible for the epileptic attack. This preferably occurs by applying a field, as explained in greater depth below.

The second applied example for avoiding an epileptic attack is presented below for more in-depth discussion.

The Dynamic Prediction Quantity

The idea is comprised is the expansion of the statistical approximation according to Schittenkopf for detecting a Markov character in which a given empirical time row is inherent. One objective is to separate a deterministic part from a stochastic part of a dynamic system is the area of statistical test theory in that the information flow of the system is analyzed. The statistical development of the dynamics is tested against a hierarchy of zero hypotheses that correspond to non-linear Markov processes with increasing order n. These processes are divided into a deterministic part and a stochastic part in the following way:

$$x_1 = f(x_{t-1}, \ldots, x_{t-n}) + u \qquad (1),$$

where u indicates an additive noise distributed according to Gauss with the variance $O^2$, $x_t$ indicates a measured datum at the time t and $f(x_{t-1}, \ldots, x_{t-n})$ indicates a deterministic part.

The Markov process with the order n is defined by the conditioned probability densities thereof $$p(x_t|x_{t-1}, \ldots, x_{t-n}) \propto \exp\left[-\frac{[x_t - f(x_{t-1}, \ldots, x_{t-n})]^2}{2\sigma^2}\right]. \qquad (2)$$

The deterministic part is implemented by a neural network NN that is trained according to the maximum likelihood principle G. Deco, D. Obradovic, "An Information-Theoretic Approach to Neural Computing", Springer-Verlag, 1996, Chapter 7.2 (Obradovic) applied to the probability densities according to Equation (2). The stochastic part u is described by noise distributed according to Gauss, where the variance $o^2$ is referred to a defined, mean last quadratic error. In other words, the zero hypotheses contain not only the order of the Markov process but also an actual deterministic structure. When a chaotic condition is present, thus, the order of the accepted zero hypothesis is the EED (effective embedding dimension). This approach opens up a method for determining the EED, whereas temporary measured data are modelled parallel to it.

This approach also allows a strict expansion of the concept of ED (embedding) when a chaotic condition prevails. The express determination of the deterministic part is a method for filtering the noise out of the time row.

The zero hypothesis is implemented with a method described in Schittenkopf.

As known from Deco and Schittenkopf, an information flow, i.e., a non-parametric criterion of a predictable development, is used as a discriminating statistic. A significance test is implemented for every point in time to be predicted, where the zero hypothesis (i.e., a given assumption that is to be checked) is only accepted when the significance test is met for all quantities of the point in time to be predicted.

Analysis of Human Epilepsy Attacks

As described above, one application of the invention is represented by the analysis of EEG measured data in order to prevent an epileptic attack. One goal is to test, in this analysis, whether a dynamic classification of the measured data for time windows of different size can be used as prediction quantities in order to predict an epileptic attack. In particular, two prediction quantities are recited:

a) The "reminder" of the underlying dynamics, i.e., the EED (see the above comments);

b) a non-parametric criterion for a predictability, defined by the integration of the information flow.

The approach presented here does not assume that the underlying dynamics are chaotic (even if they could be); rather, the emphasis lies on the time span preceding the epileptic attack in order to define a prediction quantity for the epileptic attack that is based on the dynamics of the system.

Control of the Epileptic Attack

An epileptic attack can be suppressed in that a constant electrical field is supplied to the regions that are affected by the epileptic attack (see B. Gluckmann, E. Nell, T. Netoff, W. Ditto, M. Spano, S. Schiff, "Electric field suppression of epiletiform activity in hippocampal slices", Journal of Neurophysiology 76 pages 4202–4205, 1996 (Gluckmann).

According to an assumption that the normal condition of the brain is marked by chaotic dynamics, an epileptic attack is expressed by a drastic simplification of the dynamics in the brain. The epileptic attack is countered in that the reduction of the dynamics, i.e., the synchronicity is, as described above, opposed in that a noise is supplied to the system (the brain in this case).

The delivery of this noise is preferably generated by applying an electrical field or a magnetic field in the immediate environment of (as close as possible to) the location of the action. Electrodes for generating an electrical field or coils for generating a magnetic field are preferably employed for this purpose. The synchronously firing neurons in the epileptic attack have their synchronicity disturbed by the electrical and/or magnetic field; a (seemingly) chaotic firing of the neurons is re-established in the brain, and the epileptic attack has thus been averted.

It is fundamentally important that a suitable reaction is carried out in response to an abnormal behavior of a dynamic system, by the inventive system in which the abnormal behavior is detected with a prediction quantity. Depending on the field of employment, this reaction may be, for example, generating a chaotic field or in generating a regular field. This action, which is implemented by the actuator, is dependent on the respective field of employment.

What the various versions of the method respectively have in common is a dynamic learning, in which a significant abnormality is allocated to a prediction quantity and this prediction quantity enables a detection of an impending abnormality. The methods then implement a suitable action with the actuator within a predetermined time interval preceding the occurrence of the abnormality (e.g., of the epileptic seizure or of the chaotically beating heart). The prediction quantity thus enables the recognition of an abnormality before, the abnormality actually occurs.

Since the entire system changes over a longer time span in view of its dynamically normal property, an adaption of the originally learned dynamic system is necessary. It is important to define the prediction quantity in that the data significantly characterizing an abnormality are imaged from the entire dynamic system in the prediction quantity. A prediction of the abnormality can thus ensue even given a dynamic system subject to great fluctuations, for example, a heart that is subjected to a great variety of stresses, and where one of these stresses does not necessarily indicate an abnormality.

The above-described method is illustrative of the principles of the present invention. Numerous modifications and adaptions thereof will be readily apparent to those skilled in this art without departing from the spirit and scope of the present invention.

The invention claimed is:

1. An arrangement for predicting an abnormality of a dynamic system and for implementing an action opposing the abnormality using a continuous information flow that describes a development of a predictability of several future system states, comprising:
    a) a measured data pick-up that registers comparison measured data of said system and test measured data of said system;
    b) a processor unit, having a neural network that models said system, said processor unit
        (1) training said neural network using said comparison measured data;
        (2) determining a comparison information flow that describes a comparison dynamic of said system using said trained neural network;
        (3) determining a test information flow that describes a test dynamic of said system using said test measured data;
        (4) using said comparison information flow and said test information flow, predicting said abnormality as established when said comparison information flow differs significantly from said test information flow, and predicting said abnormality as not established when said comparison information flow does not significantly differ from said test information flow;
        (5) when said abnormality of the system has been predicted as established, then implementing said action; and
    c) an actuator that implements said action,
    wherein the information flow describes a development of a predictability of plural future system states.

2. An arrangement according to claim 1, wherein said processor unit endlessly loops from said determining a comparison information flow to said implementing said action.

3. Arrangement according to claim 1, wherein said abnormality is predicted as established when said test information flow is significantly smaller than said comparison information flow.

4. An arrangement according to claim 3, wherein said action comprises exciting said system with a chaotic signal.

5. An arrangement according to claim 4, wherein said action comprises supplying noise to said system.

6. An arrangement according to claim 5, wherein said noise is supplied by a corresponding electrical field.

7. An arrangement according to claim 6, wherein said electrical field is supplied by at least one electrode.

8. An arrangement according to claim 5, wherein said noise is supplied by a corresponding magnetic field.

9. An arrangement according to claim 8, wherein said magnetic field is supplied by at least one electrode.

10. An arrangement according to claim 1, wherein said abnormality is predicted as established when said test information flow is significantly greater than said comparison information flow.

11. An arrangement according to claim 10, wherein said action comprises exciting said system with a regular signal.

12. An arrangement according to claim 11, wherein said regular signal is supplied by an electrical field.

13. An arrangement according to claim 11, wherein said electrical field is supplied by at least one electrode.

14. An arrangement according to claim 11, wherein said regular signal is supplied by a magnetic field.

15. An arrangement according to claim 14, wherein said magnetic field is supplied to said system by at least one electrode.

16. A method for predicting an abnormality of a dynamic system and for implementing an action opposing the abnormality using a continuous information flow that describes a development of a predictability of several future system states, comprising:
    a) measuring comparison measured data of said system and test measured data of said system;
    b) determining a neural network that models said system using said comparison measured data;
    c) determining a comparison information flow that describes a comparison dynamic of said system using said neural network;
    d) determining a test information flow that describes a test dynamic of said system using said test measured data;
    e) comparing said comparison information flow to said test information flow using said comparison information flow and said test information flow;
    f) determining said abnormality to be predicted as established when said comparison information flow differs significantly from said test information flow;
    g) determining said abnormality to be predicted as not established when said comparison information flows does not significantly differ from said test information flow; and
    h) implementing said action when said abnormality of said system has been predicted as established,
    wherein the information flow describes a development of a predictability of plural future system states.

17. A method for predicting an abnormality of a dynamic system using a continuous information flow that describes a development of a predictability of several future system states, comprising the steps of:
    a) measuring comparison measured data of said system and test measured data of said system;
    b) determining a comparison information flow that describes a comparison dynamic of said system using said comparison measured data;
    c) determining a test information flow that describes a test dynamic of said system using said test measured data;
    d) comparing said comparison information flow to said test information flow using said comparison information flow and said test information flow;
    e) determining said abnormality to be predicted as established when said comparison information flow differs significantly from said test information flow; and f) determining said abnormality to be predicted as not established when said comparison information flow does not significantly differ from said test information flow, wherein the information flow describes a development of a predictability of plural future system states.

18. A method for predicting an abnormality of a dynamic system and for implementing a procedure in response to the abnormality, comprising:

training a neural network to learn the dynamics of a system;

evaluating a continuous information flow received from the system;

predicting an abnormality when the information flow differs significantly from normal state information as determined by the neural network; and implementing a procedure, if an abnormality is predicted, to prevent or treat the abnormality, wherein the information flow describes a development of a predictability of plural future system states.

* * * * *